(12) United States Patent
Dupre

(10) Patent No.: US 6,899,883 B2
(45) Date of Patent: *May 31, 2005

(54) TREATMENT OF DIABETES

(75) Inventor: John Dupre, London (CA)

(73) Assignee: London Health Sciences Centre, London (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/737,446
(22) PCT Filed: May 12, 1995
(86) PCT No.: PCT/CA95/00287
§ 371 (c)(1),
(2), (4) Date: Jan. 10, 1997
(87) PCT Pub. No.: WO95/31214
PCT Pub. Date: Nov. 23, 1995

(65) Prior Publication Data
US 2002/0119146 A1 Aug. 29, 2002

(30) Foreign Application Priority Data
May 12, 1994 (GB) .............................. 9409496

(51) Int. Cl.[7] ................................ A61K 1/00
(52) U.S. Cl. .................................. 424/198.1
(58) Field of Search .......................... 514/13; 530/308; 474/198.1

(56) References Cited

U.S. PATENT DOCUMENTS 5,424,286 A * 6/1995 Eng .............................. 514/2

FOREIGN PATENT DOCUMENTS

| EP | 0044168 | | 1/1982 |
| EP | 708179 | A3 | 4/1996 |
| GB | 94 09496.8 | B | 5/1994 |
| WO | WO 90/11296 | | 3/1989 |
| WO | WO 91/11457 | | 8/1991 |
| WO | WO93/18786 | * | 9/1993 |
| WO | 93/18786 | | 9/1993 |
| WO | WO 93/18786 | | 9/1993 |
| WO | WO 93/25579 | | 12/1993 |

OTHER PUBLICATIONS

Kumar et al., P.N.A.S. USA, vol. 87:1337–1341, Feb. 1990.*
Gutniak et al., N.E.J.M., vol. 326: 1316–1322, May 1992.*
D'Alessio et al. J.C.I. vol. 93: 2263–2266, May 1994.*
Ngo, The Protein Folding Problem and Tertiam, Structure Prediction, 1994, Merz et al. (ed.) Binkhauser, Boston pp. 433, 492–495.*

Goth, Medical Pharmacology, Principles and Concepts Mosby Co. St Louis p. 184 pp. 19–20, 1984.*
Stedman's Medical Dictionary 24th Edition Williams & Wilkins, pp. 34 & 60, 1988.*
Andrews, et al, "Isolation and structures of Glucagon and Glucagon–like peptide from catfish pancreas," *Journal of Biological Chemistry* 260:3910–3914 (1985).
Bell, et al, "Hamster preproglucagon contains the sequence of glucagon and two related peptides," *Nature* 302:716–718 (1983).
D'Alessio, D.A., et al. "Glucagon–like Peptide 1 Enhances Glucose Tolerance Both by Stimulation of Insulin Release and by Increasing Insulin–independent Glucose Disposal," *J. Clin. Invest.*, 93:2263–2266 (1994).
Faloona, G.R., et al, in *Methods of Hormone Radioimmunoassay*, Unger, B.M. (eds), Academic Press, NY, pp. 317–330 (1974).
Ghiglione, et al, "How Glucagon–Like is Glucagon–Like peptide?" *Diabetologia* 27:599–600 (1984).
Goth, *Medical Pharmacology: Principles and Concepts,* Mosby Co., St. Louis, pp. 19–20 (1984).
Gutniak, M., et al, "Antidiabetogenic effect of glucagon–like peptide–1 (7–36) amide in normal subjects and patients with diabetes mellitus," *New England Journal of Medicine* 326(20):1316–1322 (1992).
Kreymann, B., et al, "Glucagon–like peptide–1 7–36: A physiological incretin in man," *Lancet* 2:1300–1304 (1987).
Kumar, V., et al, "Amino acid variations at a single residue in an autoimmune peptide profoundly affect its properties: T–cell activation, major histocompatibility complex binding, and ability to block experimental allergic encephalomyelitis," *Proc. Natl. Acad. Sci.* 87:1337–1341 (1990).
Nathan, D.M., et al, "Insulinotropic Action of Glucagonlike Peptide–1–(7–37) in Diabetic and Nondiabetic Subjects," *Diabetes Care* 15:270–276 (1992).
Ngo, J.T., in *The Protein Folding Problem and Tertiary Structure Prediction,* Merz (ed), Birkhauser Boston, pp. 492–495 (1992).
Schmidt, et al, "Glucagon–Like peptide–1 but not Glucagon–like peptide–2 stimulates insulin release from isolated rat pancreatic islets," *Diabetologia* 28:704–707 (1985).
Uttenthal, et al, "Molecular forms of Glucagon–like peptide–1 in human pancreas and Glucagonomas," *The Journal of Clinical Endocrinology and Metabolism* 61:472–479 (1985).
Wettergren, et al, "Trucated GLP–1 (Proglucagon 78–107–Amide) inhibits gastric and pacreatic functions in man," *Dig Dis Sci* 38:665–673 (1993).

(Continued)

Primary Examiner—Patrick J. Nolan
(74) Attorney, Agent, or Firm—Sim & McBurney

(57) ABSTRACT

The present invention provides a method of treating insulin-requiring diabetes in a mammal comprising the subcutaneous administration of an effective amount of a glucagon-like peptide 1-related peptide.

11 Claims, 10 Drawing Sheets

OTHER PUBLICATIONS

Gutniak et al., "Antidiabetogenic Effect of Glucagon–like Peptide–1 (7–36)Amide In Normal Subjects and Patients with Diabetes Mellitus," *N.E.J.M.* 326:1316 (1992).

Wettergren et al., "Truncated GLP–1 (Proglucagon 78–107–Amide) Inhibits Gastric and Pancreatic Functions in Man," *Digestive Diseases and Sciences* 38:665 (1993).

Fehmann, et al., "Insulinotropic Hormone Glucagon–like Peptide–1(7–37) Stimulation of Proinsulin Gene Expression and Proinsulin Biosynthesis in Insulinoma Beta TC–1 Cells," *Endocrinology*, 130(1):159–66 (1992).

Gromada, et al., "Desensitization of Glucagon–like Peptide 1 Receptors in Insulin–secreting βTC3 Cells: Role of PKA–independent Mechanisms, " *Brit. Jour. Phar.*, 118:769–75 (1996).

Gromada, et al., "Cellular Regulation of Islet Hormone Secretion by the Incretin Hormone Glucagon–like Peptide 1," *Eur. J. Physiol.*, 435:583–94 (1998).

Jones, et al., "Effects of Fedotozine on Gastric Emptying and Upper Gastrointestinal Symptoms in Diabetic Gastroparesis," *Ailment. Pharmacol. Ther.*, 14:937–43 (2000).

* cited by examiner

TREATMENT OF DIABETES

FIELD OF THE INVENTION

The present invention relates to methods and compositions for treatment of diabetes.

BACKGROUND OF THE INVENTION

The recent findings of the Diabetes Control and Complications Trial (DCCT) carried out by the U.S. National Institute of Health have emphasised the importance of doing everything possible to normalise blood glucose levels in diabetics to avoid or delay micro-vascular damage. Intensified insulin therapy has been-shown by the trial to improve glycaemic control but is accompanied by the risk of hypoglycaemia. This limits the degree of glycaemic control which can be safely attempted, so that true normalisation of blood glucose levels cannot be achieved with insulin therapy alone.

Glucagon-like peptide 1(7–36) amide or glucagon-like insulinotropic peptide (GLIP) is a gastrointestinal peptide which potentiates insulin release in response to glycaemia in normal humans.

Glucagon-like insulinotropic peptide has been suggested for use either alone or in conjunction with oral hypoglycaemic agents in Type II or non-insulin dependent diabetes (Gutniak et al., (1992), N.E.J.M. vol. 326, p. 1316; International Patent Application No. WO93/18786). These authors have noted a synergistic effect between the peptide and oral hypoglycaemic agents in Type II diabetics.

The present inventor has found, unexpectedly, that administration of glucagon-like insulinotropic peptide permits improved glycaemic control in subjects with insulin-requiring diabetes.

SUMMARY OF THE INVENTION

In accordance with one embodiment of the present invention, a method is provided for treating insulin-requiring diabetes in a mammal comprising administering to the mammal in a suitable regimen an effective amount of insulin and an effective amount of a peptide comprising a peptide selected from the group consisting of
  (a) glucagon-like peptide 1(7–37);
  (b) glucagon-like peptide 1(7–36)amide; and
  (c) an effective fragment or analogue of (a) or (b).

In accordance with a further embodiment of the invention, a peptide comprising a peptide selected from the group consisting of
  (a) glucagon-like peptide 1(7–37);
  (b) glucagon-like peptide 1(7–36)amide; and
  (c) an effective fragment or analogue of (a) or (b) is used for the preparation of a medicament for use in the treatment of insulin-requiring diabetes in a suitable regimen which additionally comprises treatment with insulin.

In accordance with a further embodiment of the invention, a peptide comprising a peptide selected from the group consisting of
  (a) glucagon-like peptide 1(7–37);
  (b) glucagon-like peptide 1(7–36)amide; and
  (c) an effective fragment or analogue of (a) or (b) is used for the preparation of a medicament which also includes insulin for treatment of insulin-requiring diabetes.

In accordance with a further embodiment of the invention, a pharmaceutical composition is provided for the treatment of insulin-requiring diabetes comprising an effective amount of a peptide comprising a peptide selected from the group consisting of
  (a) glucagon-like peptide 1(7–37);
  (b) glucagon-like peptide 1(7–36)amide; and
  (c) an effective fragment or analogue of (a) or (b) and a pharmaceutically acceptable carrier.

In accordance with a further embodiment of the invention, a method is provided for treating Type I diabetes in a mammal comprising administering to the mammal an effective amount of a peptide comprising a peptide selected from the group consisting of
  (a) glucagon-like peptide 1(7–37);
  (b) glucagon-like peptide 1(7–36)amide; and
  (c) an effective fragment or analogue of (a) or (b).

In accordance with a further embodiment of the invention, a peptide comprising a peptide selected from the group consisting of
  (a) glucagon-like peptide 1(7–37);
  (b) glucagon-like peptide 1(7–36)amide; and
  (c) an effective fragment or analogue of (a) or (b) is used for the preparation of a medicament for use in the treatment of Type I diabetes.

DETAILED DESCRIPTION OF THE INVENTION

The glucagon-like peptide 1 fragments, glucagon-like peptide 1(7–36)amide and glucagon-like peptide 1(7–37), show essentially similar insulinotropic and other biochemical effects in humans and other mammals.

Glucagon-like peptide 1(7–36)amide is referred to herein as GLIP.

The present invention provides a method of treating Type I diabetes by administration of an effective amount of GLIP, or other glucagon-like peptide 1-related peptide, either alone or in conjunction with a regimen of insulin administration.

Although the discussion herein refers to use of "GLIP", it will be understood by those skilled in the art that the therapeutic methods of the invention may be practised by employing GLIP, glucagon-like peptide 1(7–37), an effective peptide including GLIP or glucagon-like peptide 1(7–37), or an effective fragment or analogue of GLIP or glucagon-like peptide 1(7–37).

Figure 1A:
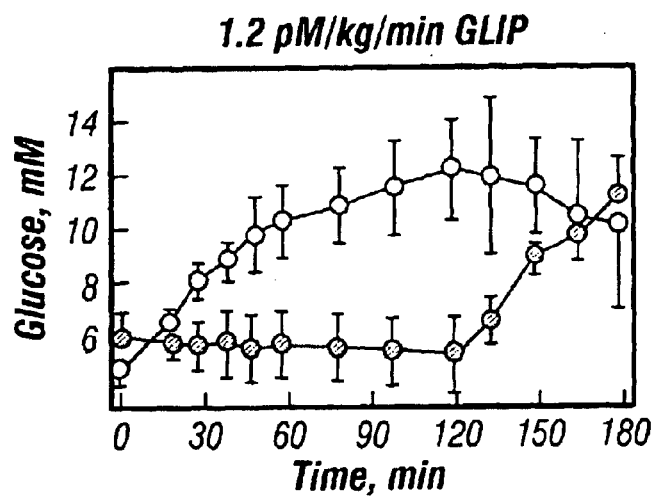
FIG. 1A shows blood levels of glucose.
Figure 1B:
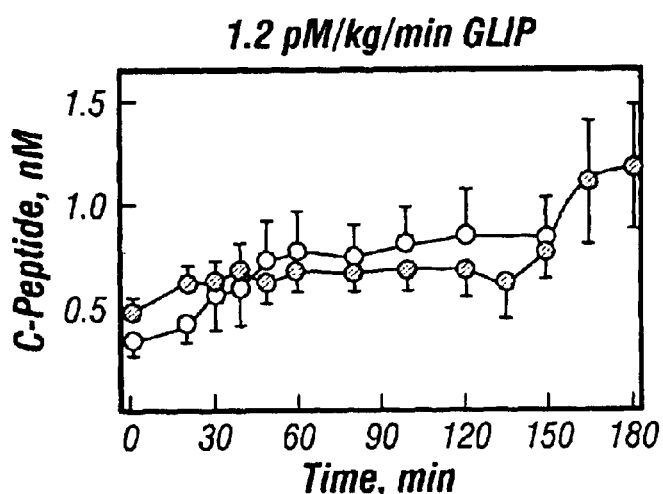
FIG. 1B shows ;-peptide.
Figure 1C:
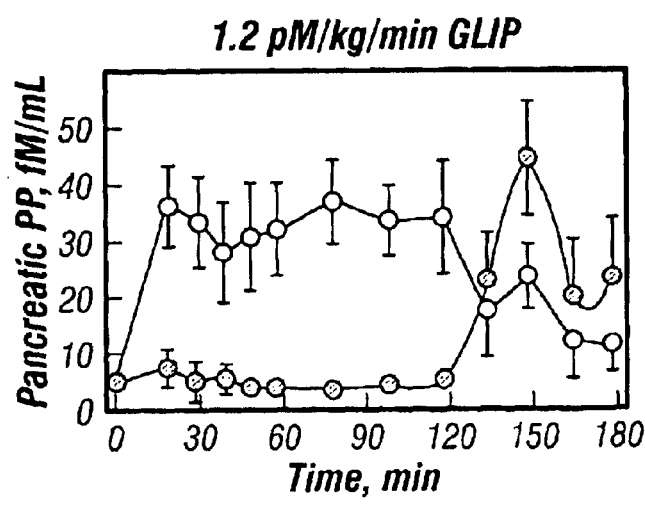
FIG. 1C shows human pancreatic polypeptide (HPP)
Figure 1D:
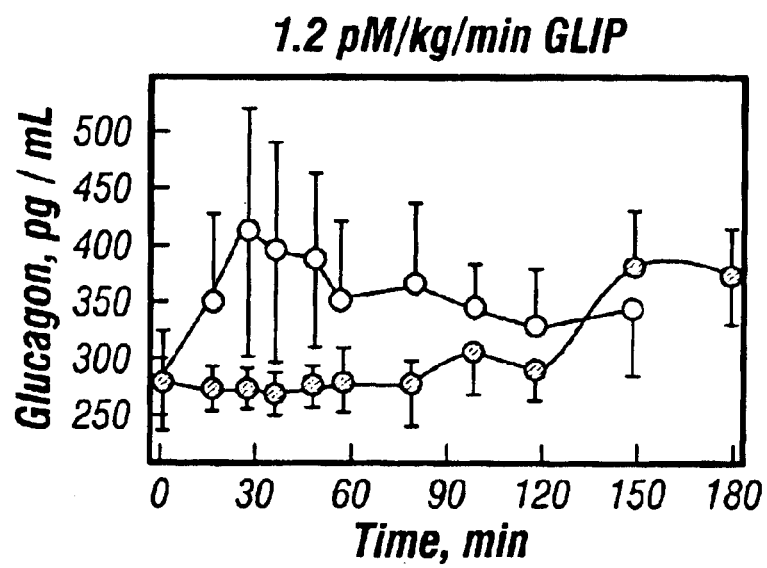
FIG. 1D shows glucagon and FIG. 1E shows gastrin in Type I diabetic subjects after Sustacal meal alone (○) or Sustacal meal with GLIP infusion (●).
Figure 1E:
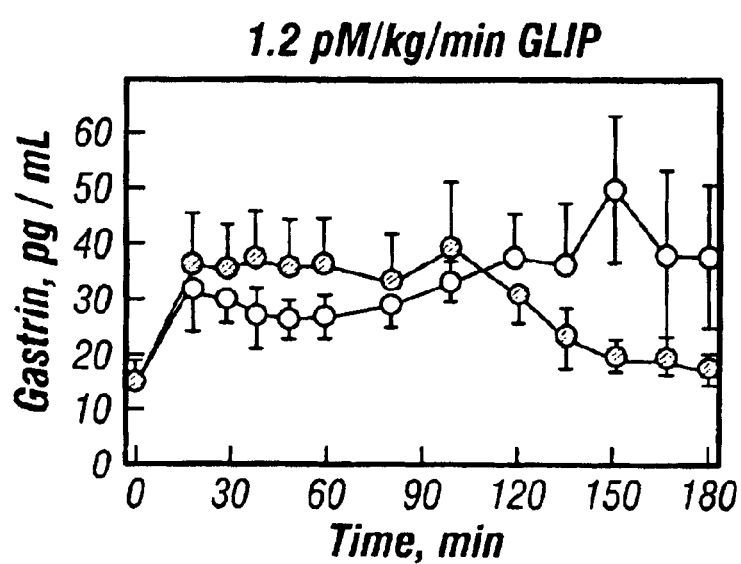
Figure 2A:
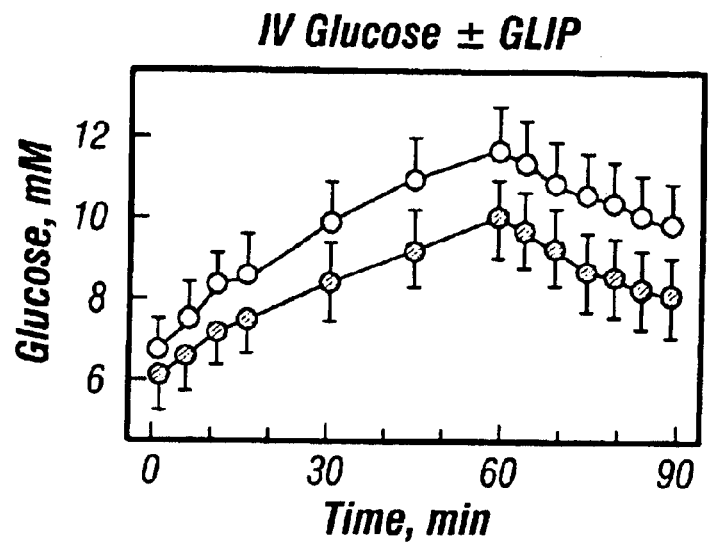
FIG. 2A shows blood levels of glucose and FIG. 2B C-peptide in Type I diabetic subjects during glucose infusion alone (○) or along with IV GLIP(●).
Figure 2B:
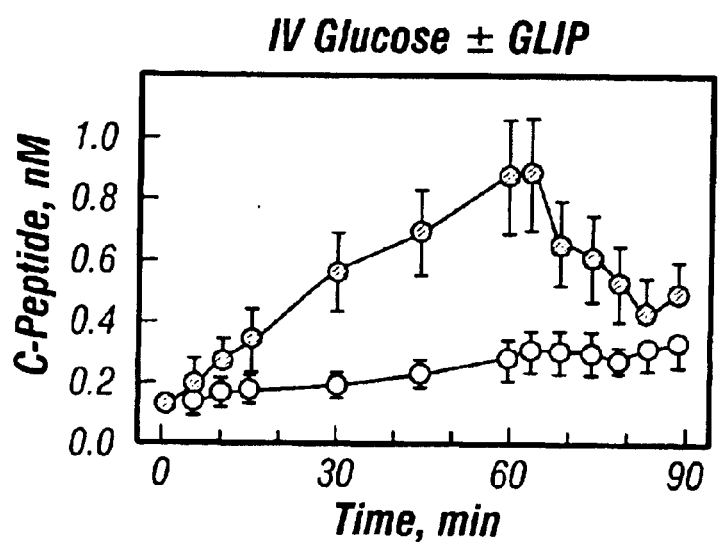

As is seen in FIG. 2, IV administration of GLIP along with intravenous glucose stimulated secretion of endogenous insulin in the subjects studied and gave improved control of blood glucose level. These subjects were in the remission phase, or so-called "honeymoon phase", of IDDM characterised by substantial remaining endogenous insulin secretion.

The same dose of GLIP (1.2 pm/kg/min) gave excellent control of blood glucose level in these subjects after a meal, as seen in FIG. 1, Panel A. Under theses conditions, GLIP infusion also prevented a significant increase in blood levels of C-peptide.

After the Sustacal meal, the test subjects showed normal secretion of pancreatic polypeptide (PP) but this response was absent during GLIP infusion (FIG. 1, Panel C). It is believed that this abrogation of PP response was due to the delayed passage of the meal from the stomach to the small intestine as a result of GLIP administration. That it was not due to a general suppression of gastrointestinal peptide secretion is indicated by the normal gastrin response to the presence of food in the stomach in These subjects (FIG. 1, Panel E).

Administration of GLIP prevented the mean rise in plasma glucagon levels stimulated by the meal in the absence of GLIP. Gastrin levels ware not significantly affected.

Figure 3A:
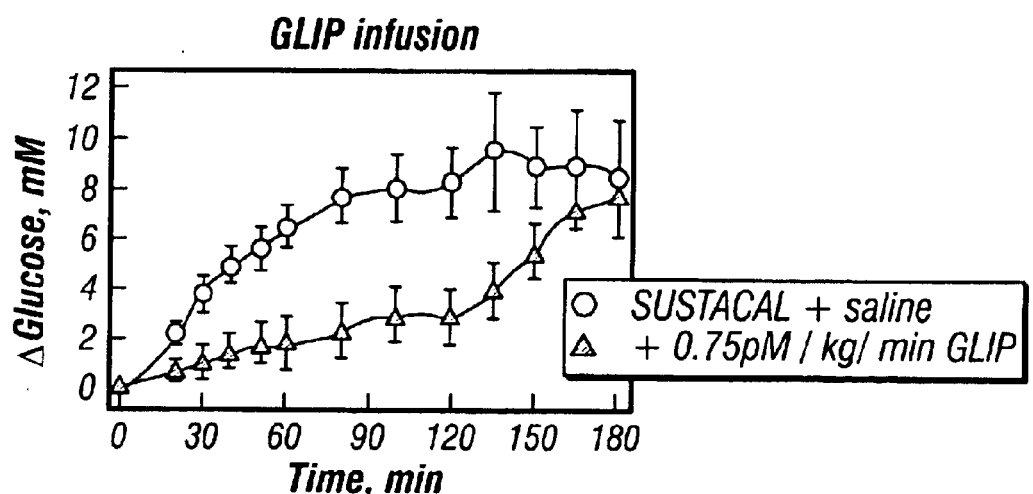
FIG. 3A shows blood levels of glucose (expressed as the change (Δ) from baseline values at time zero) and FIG. 3B shows C-peptide (expressed as the change (Δ) from baseline values at time zero) in Type I diabetic subjects after Sustacal meal and saline infusion (○) or Sustacal meal with infusion of 0.75 pm GLIP/kg/min (▲).
Figure 3B:
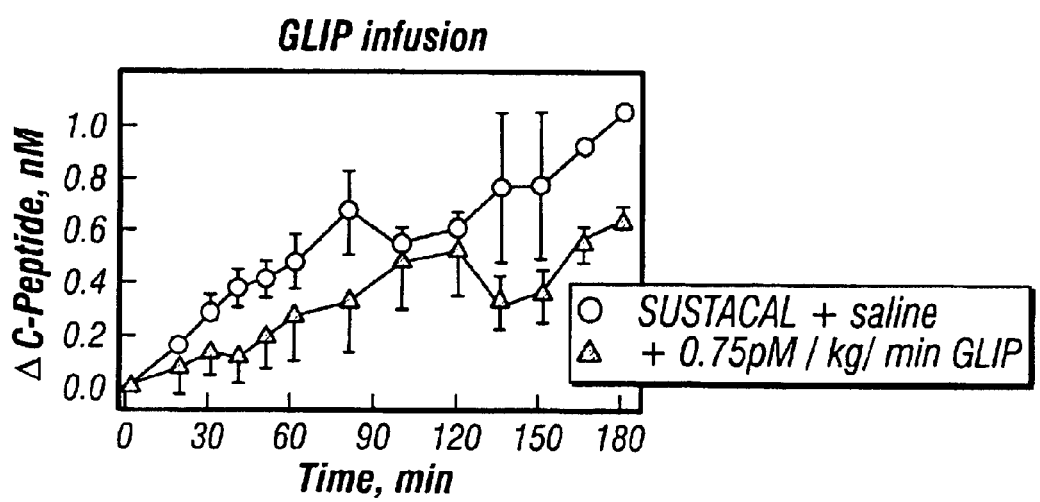
Figure 4A:
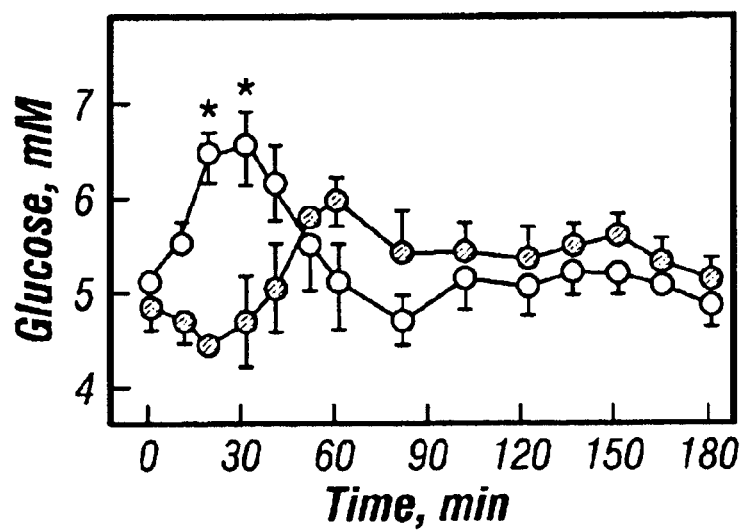
FIG. 4A shows blood levels of glucose.
Figure 4B:
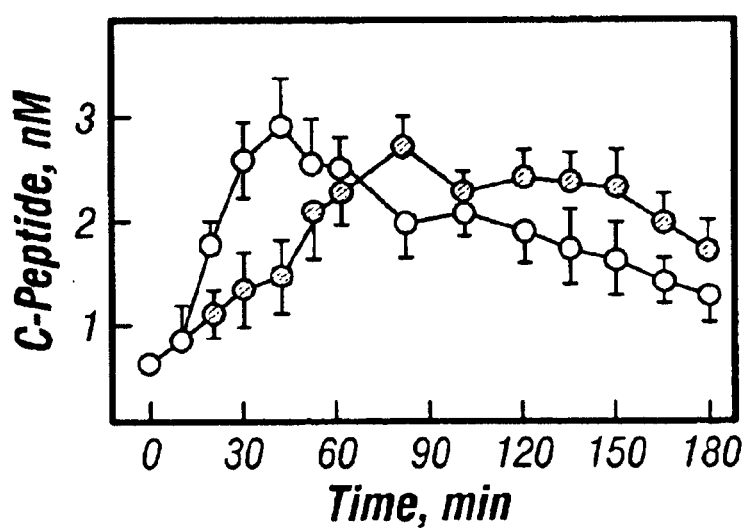
FIG. 4B shows C-peptide.
Figure 4C:
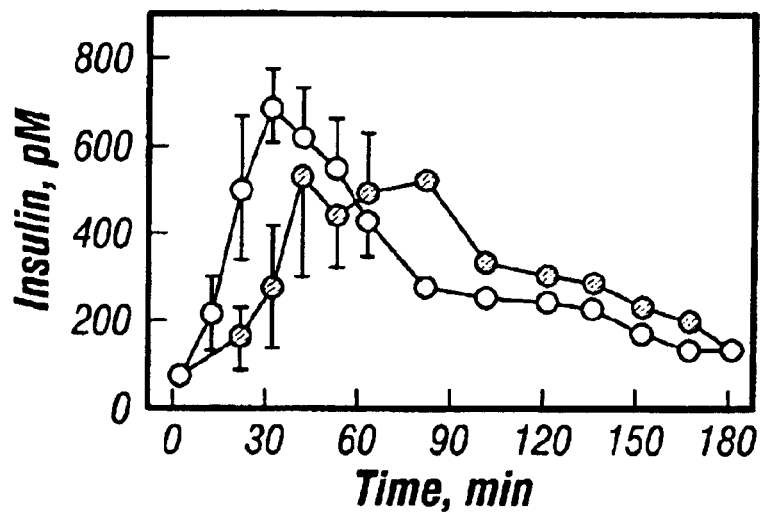
FIG. 4C shows insulin and FIG. 4D shows human pancreatic polypeptide (HPP) in normal subjects after Sustacal meal alone (○) or Sustacal meal immediately preceded by a subcutaneous injection of 100 μg GLIP (●).
Figure 4D:
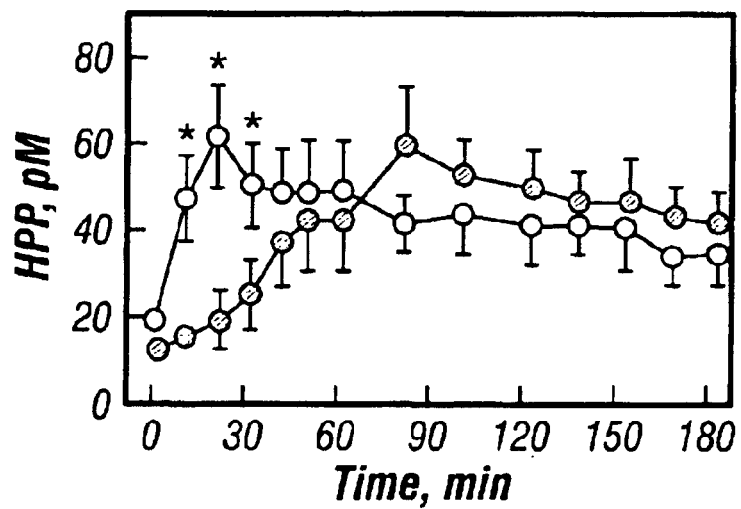
Figure 5A:
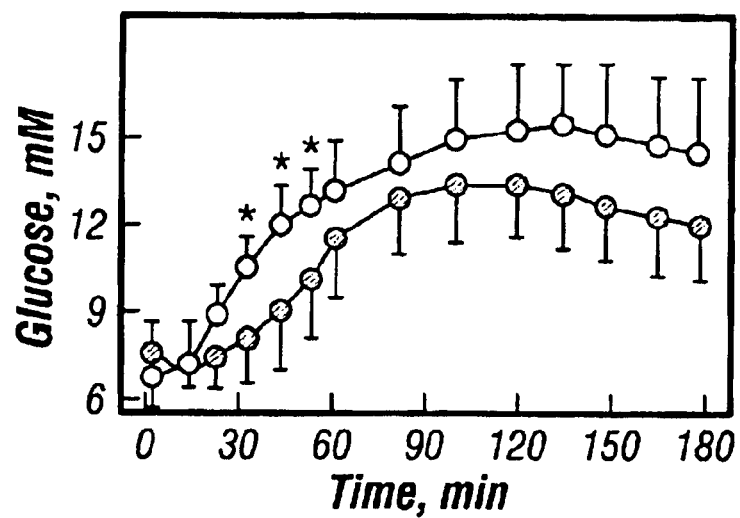
FIG. 5A shows blood levels of glucose.
Figure 5B:
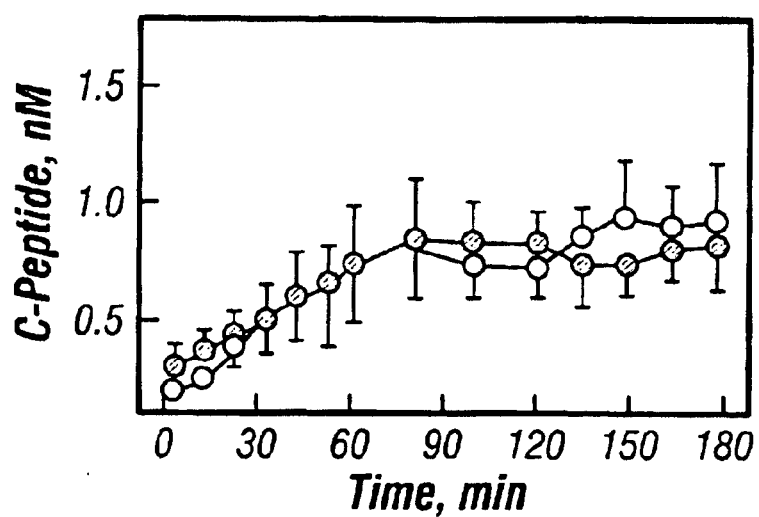
FIG. 5B shows C-peptide.
Figure 5C:
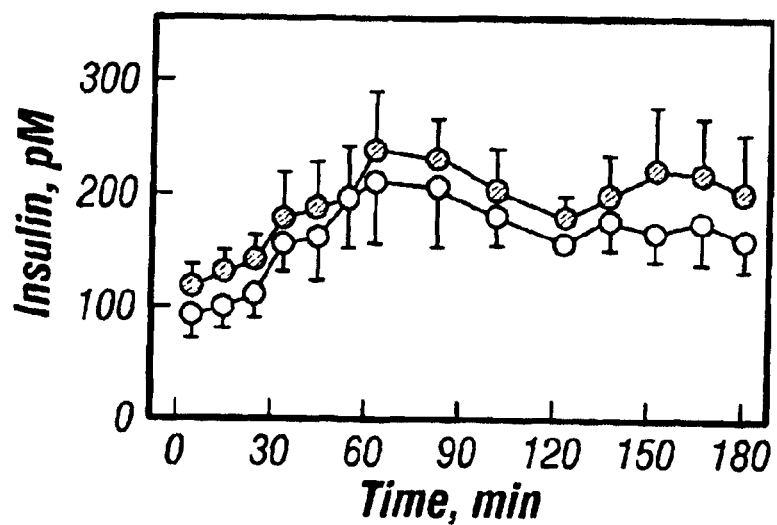
FIG. 5C shows insulin and FIG. 5D shows human pancreatic polypeptide (HPP) in Type I diabetic subjects after Sustacal meal alone (○) or, Sustacal meal immediately preceded by a subcutaneous injection of 100 μg GLIP (●).
Figure 5D:
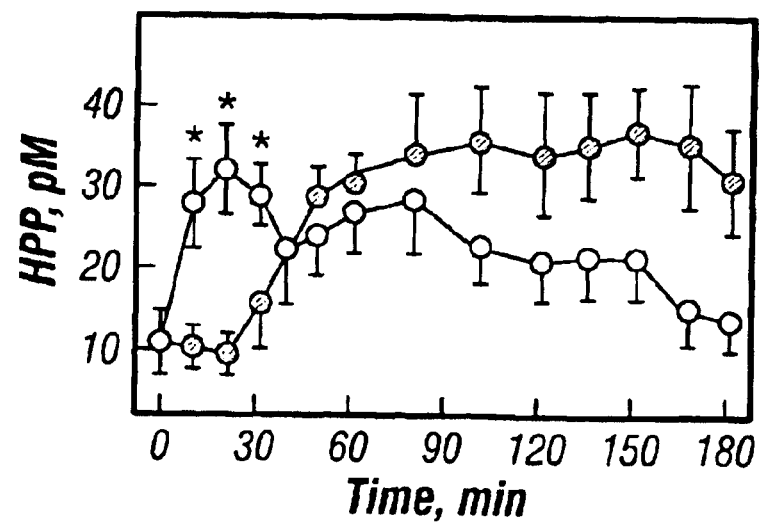
Figure 6A:
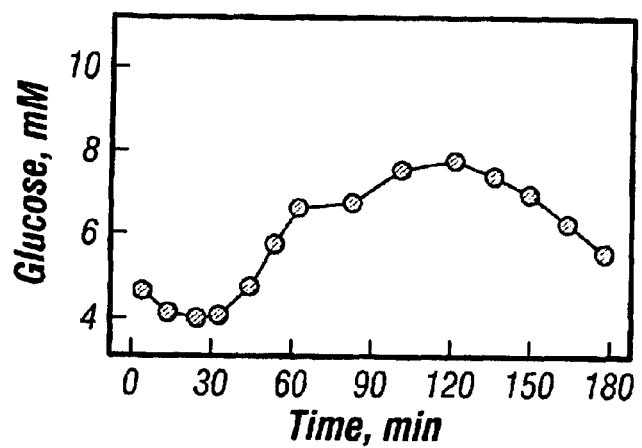
FIG. 6A shows blood levels of glucose.
Figure 6B:
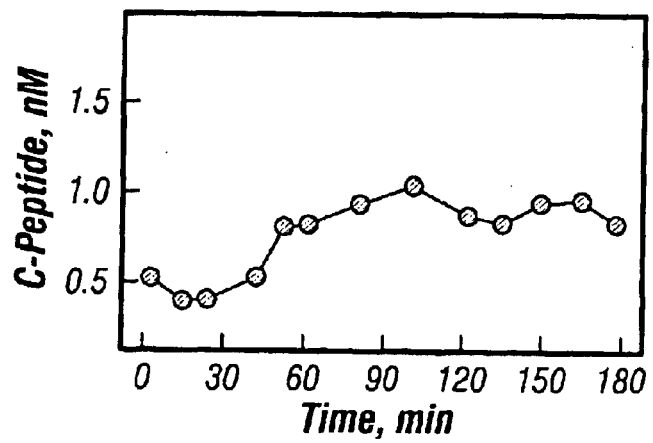
FIG. 6B shows C-peptide.
Figure 6C:
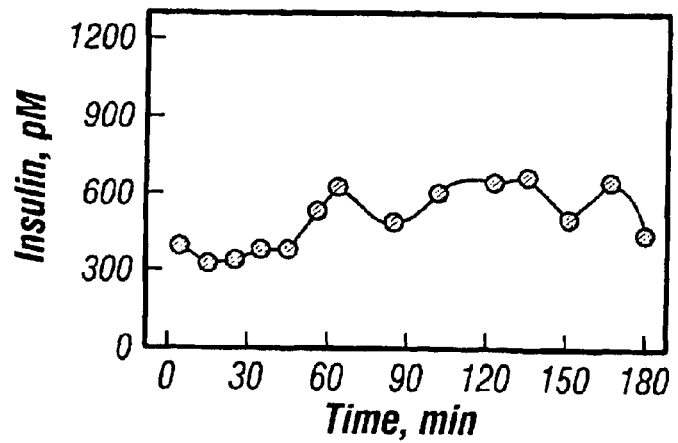
FIG. 6C shows insulin.
Figure 6D:
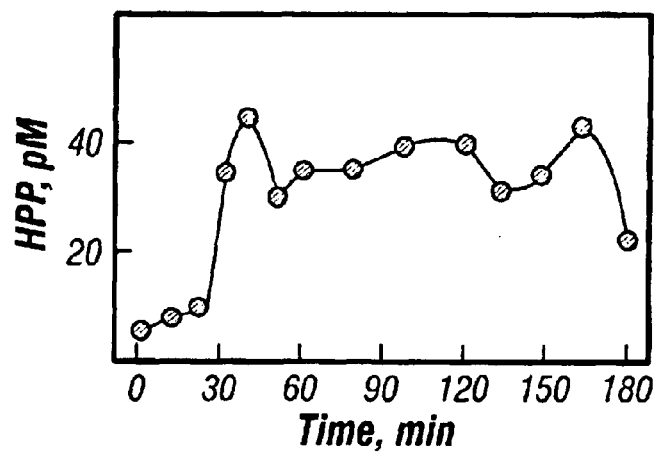
FIG. 6D shows human pancreatic polypeptide (HPP), FIG. 6E hows GLIP (GLIP-1) and FIG. 6F gastrin in a Type I diabetic subject who received 5 Units regular human insulin and 50 μg GLIP subcutaneously prior to a Sustacal meal.
Figure 6E:
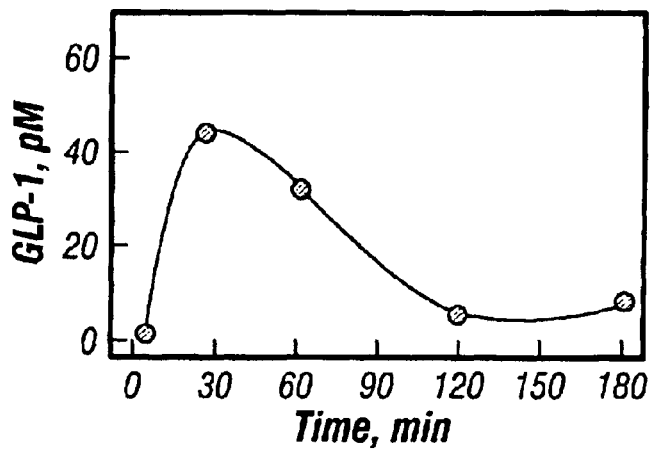
Figure 6F:
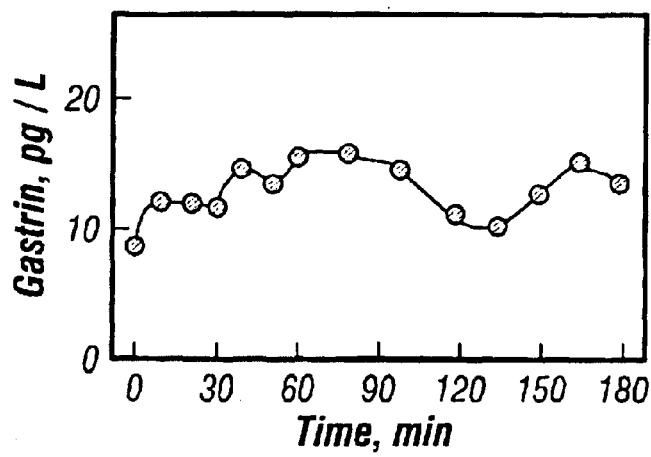

Administration of a lower dose of GLIP (0.75 pmol/kg/min) along with a meal resulted in some-increase in blood glucose and C-peptide, as seen in FIG. 3. Although the increase in glucose was less than in the control experiment, the rise in C-peptide was similar to the control experiment.

GLIP is known to cause delay of gastric emptying in humans and other mammals (Wettergren et al., (1993), Digestive Diseases and Sciences, v. 38, p. 665). As seen in FIG. 4, when GLIP is given subcutaneously to normal subjects prior to ingestion of a meal, there is a delay of 30 to 60 minutes in the rise in blood glucose level. This delay is likely due to inhibition of gastric emptying.

When Type I diabetics were given GLIP subcutaneously prior to ingestion of a test meal, a lowering of blood glucose levels was seen compared to the control figures when no GLIP was administered (FIG. 5, Panel A). The delayed rise in pancreatic polypeptide (HPP) levels (Panel D) indicate delayed gastric emptying. As,seen from Panels B and C, there was no enhancement of insulin secretion over control levels to account for the lower glucose levels.

It may be that the improved glycaemic control seen with GLIP administration in Type I diabetics is due to delay of the post-meal rise in blood glucose through the interval required for the establishment of the effect of insulin.

The efficacy of GLIP administration along with insulin in restraining the expected rise in blood glucose after a standard meal in Type I diabetes is seen in Example 6 and FIG. 6. 50 μg GLIP was administered along with half the insulin dose that would usually be required to deal with the test meal. As seen in FIG. 6, Panel A, blood glucose did not rise above 8 mM. With this size of meal and half the usual insulin dose, considerably higher blood glucose levels would have been expected, in the absence of the effect of GLIP. For example, with this meal and no insulin, blood glucose levels reached 15 mM, as seen in FIG. 5, Panel A.

As seen from FIG. 6, Panel E, GLIP was cleared from the blood in about two hours so that pre-meal GLIP administration would not be expected to interfere with management of subsequent meals.

When GLIP is used to improve glycaemic control in Type I diabetics having residual endogenous insulin secretion capacity, both the insulinotropic effect of the hormone and its effect to delay gastric emptying will contribute to its effect. Some remission phase Type I subjects may be sufficiently controlled by administration of GLIP alone, without exogenous insulin.

In the majority of patients with Type I diabetes, however, treatment with a regimen including both GLIP and insulin is likely to be required. These studies indicate that the observed effects of GLIP on glycaemia are not dependent on stimulation of insulin release and are therefore not limited to diabetics retaining residual insulin secreting capacity.

The use of GLIP in treating Type I diabetes, in accordance with the present invention, provides improved glycaemic control and reduces post-prandial excursions of blood glucose. This accords with the current emphasis on normalising blood glucose levels as much as possible, to reduce diabetic complications.

Furthermore, a regimen combining administration of insulin and administration of GLIP, in accordance with the present invention, is applicable to patients with insulin requiring diabetes which would not strictly be classified as Type I.

An insulin-requiring diabetic is a diabetic who is unable to avoid hyperglycaemia without the use of insulin. The invention further provides a method for treating patients with diabetes which is etiologically Type II but requires insulin treatment.

Diabetics frequently find the requirements for food intake and insulin administration at midday particularly irksome and an interference with work and other activities. By administering GLIP to diabetic subjects at breakfast time, along with administration of longer acting insulin if necessary, diabetics may be able to omit lunch or greatly reduce the size of that meal, and thereby avoid the need for midday insulin.

The delayed adsorption of nutrients when both GLIP and insulin are administered before breakfast will also reduce the risk of hypoglycaemia if lunch is delayed.

The studies described herein also indicate that a therapeutic regimen including both GLIP and insulin will in many cases permit the use of reduced doses of insulin. This is also beneficial in the avoidance of hypoglycaemia.

GLIP or its related peptides which may be employed in the treatment methods described herein may be administered orally, nasally or parenterally. Parenteral administration may be by a variety of routes including subcutaneous or intravenous infusion, and subcutaneous or intravenous injection.

The regimen of GLIP or GLIP and insulin administration required to give the desired glycaemic control in a diabetic patient can be readily determined by those skilled in the management of diabetic patients.

As will be understood by those skilled in the art, any suitable insulin preparation may be used in conjunction with GLIP administration in the combined regimen described herein.

Suitable insulins include regular or fast-acting insulin to maintain blood glucose control through the post-prandial interval, with or without addition of longer-acting insulin to maintain blood glucose control through the post-absorptive interval.

The dosages of GLIP required may be optimised for each subject by evaluation of the degree of glycaemic control achieved by trial doses.

Another convenient method of monitoring the level of effect of GLIP on a subject is to monitor the blood level of pancreatic polypeptide in response to trial doses of GLIP.

Such dosage and regimen adjustments are now commonplace, for example for diabetics treated with mixtures of fast and slow acting insulins. These mixed preparations are available in various ratios of fast to slow and an appropriate ratio must be selected for a particular patient by trial doses. One patient may even employ insulin preparations of different ratios to handle varying sizes of meals. By similar testing, a suitable GLIP and insulin regimen may be selected.

GLIP and insulin may be administered separately or may be prepared and administered as a single formulation.

EXAMPLES

Example 1

7 subjects with remission phase Type I diabetes were studied after ingestion of a standardised meal of Sustacal (Upjohn) (delivering 30 kg/kg). Subjects continued their normal insulin treatment programme on the day prior to the test and, on the day of the test, omitted their morning insulin injection and arrived fasting at 8:00 am. On one test day they were given the Sustacal meal, followed immediately by initiation of intravenous infusion of GLIP (synthetic human GLIP-(7–36)amide from Peninsula, U.K.) at an infusion rate of 1.2 pm/kg/min. Infusion was continued for 120 minutes. Blood levels of glucose, C-peptide, gastrin, glucagon and HPP were monitored by standard radioimmunoassay methods in samples taken before and at intervals during the study, up to 180 minutes. On another test day, subjects were given the Sustacal meal alone and the same analytes were similarly monitored.

Results are shown in FIG. 1.

Example 2

Four subjects with remission phase Type I diabetes were studied during intravenous glucose infusion. Subjects prepared for the tests as described in Example 1, but received an intravenous infusion of glucose (20 g over 60 min. constant rate instead of the Sustacal meal. On one test day, they also received intravenous GLIP for 60 minutes (1.2 pm/kg/min for 60 min.) and on another test day, they received IV glucose alone. Blood levels of glucose and C-peptide were monitored as in Example 1.

The results are shown. in FIG. 2.

Example 3

Four subjects with remission phase Type I diabetes were studied during infusion with 0.75 pm/kg/min-GLIP for 120 minutes after a Sustacal meal.

The test was conducted as described in Example 1 and blood glucose and C-peptide levels were measured. On a further test day, the subjects were studied during saline infusion after a similar Sustacal meal.

Results are shown in FIG. 3.

Example 4

7 normal volunteers were studied after ingestion of a Sustacal meal either alone or immediately preceded by a subcutaneous injection of 100 µg GLIP.

Results are shown in FIG. 4. *indicates statistically significant differences between treatments ($p<0.05$).

A delay in increase in blood levels of glucose, HPP, C-peptide and insulin was seen. When the experiment was repeated with 50 µg or 200 µg dose of GLIP, proportionally shorter and longer delays, respectively, were seen.

Example 5

7 Type I diabetic subjects were studied. Subjects omitted their morning insulin injection on the days of the tests and were given a Sustacal meal alone one day and, on another day, a Sustacal meal immediately preceded by a subcutaneous injection of 100 µg GLIP.

The results are shown in FIG. 5. *indicates statistically significant differences between treatments ($p<0.05$).

Example 6

One Type 1 diabetic subject was given GLIP along with insulin and the effects on post-prandial glycaemia observed. The subject received 5 units of insulin and 50 µg GLIP as subcutaneous injections immediately prior to ingestion of a Sustacal meal as described in Example 1. The results are shown in FIG. 6. Blood levels of GLIP were monitored by a standard radioimmunoassay method.

Although only preferred embodiments of the present invention have been described, the present invention is not limited to the features of these embodiments, but includes all variations and modifications within the scope of the claims.

I claim:

1. A method of treating Type I diabetes mellitus in a mammal comprising administering to said mammal an effective amount of an insulin and an effective amount of glucagon-like peptide 1(7–36) amide analogue, wherein said glucagon-like peptide 1(7–36) amide analogue is administered subcutaneously.

2. A method according to claim 1, wherein said mammal is a human.

3. A method according to claim 2, wherein said insulin and said glucagon-like peptide 1(7–36) amide analogue are administered to the human at a selected time prior to ingestion of a meal.

4. A method according to any of claims 1–3, wherein said glucagon-like peptide 1(7–36) amide analogue is a glucagon-like peptide 1(7–36).

5. A method according to any of claims 1–3, wherein said glucagon-like peptide 1(7–36) amide analogue is glucagon-like peptide 1(7–37).

6. A method of treating Type I diabetes mellitus in a mammal, the method consisting essentially of administering an effective amount of glucagon-like peptide 1(7–36) amide analogue wherein said glucagon-like peptide 1(7–36) amide analogue is administered subcutaneously.

7. A method according to claim 6, wherein said mammal is a human.

8. A method according to claim 7, wherein said glucagon-like peptide 1(7–36) amide analogue is administered to the human at a selected time prior to ingestion of a meal.

9. A method according to any of claims 6–8, wherein said glucagon-like peptide 1(7–36) amide analogue is glucagon-like peptide 1(7–37).

10. A method according to any of claims 6–8, wherein said glucagon-like peptide 1(7–36) amide analogue is glucagon-like peptide 1(7–36).

11. A method of treating Type I diabetes mellitus in a mammal comprising administering to said mammal an effective amount of insulin and a peptide selected from the group consisting of:

(a) glucagon-like peptide 1(7–37);
(b) glucagon-like peptide 1(7–36) amide; and
(c) an effective fragment or analogue of (a) or (b).

* * * * *